US006376250B1

(12) United States Patent
Mohtadi

(10) Patent No.: US 6,376,250 B1
(45) Date of Patent: Apr. 23, 2002

(54) COMPOSITION AND PROBE FOR DETECTION OF WATER

(76) Inventor: Nabil J. Mohtadi, 413 Joan St., South Plainfield, NJ (US) 07080

( * ) Notice: Subject to any disclaimer, the term of this patent is extended or adjusted under 35 U.S.C. 154(b) by 111 days.

(21) Appl. No.: 09/641,269

(22) Filed: Aug. 17, 2000

(51) Int. Cl.⁷ .................. G01N 33/18; G01N 31/22; C09K 3/00
(52) U.S. Cl. ............... 436/40; 436/39; 436/60; 436/166; 252/408.1; 252/963; 73/73; 516/111; 422/57
(58) Field of Search ............. 516/111; 436/39, 436/40, 60, 164, 166; 252/408.1; 73/73; 422/57

(56) References Cited

U.S. PATENT DOCUMENTS

| | | | |
|---|---|---|---|
| 2,520,993 A | | 9/1950 | Berger .................. 436/40 |
| 2,968,940 A | * | 1/1961 | Feldman et al. ........... 73/73 |
| 3,505,020 A | | 4/1970 | Caldwell ................ 436/40 |
| 3,716,494 A | * | 2/1973 | Molina ................. 516/104 |
| 3,873,271 A | | 3/1975 | Young ................... 436/40 |
| 4,578,357 A | | 3/1986 | Melpolder .............. 436/39 |
| 4,699,885 A | | 10/1987 | Melpolder .............. 436/39 |
| 4,717,671 A | | 1/1988 | Melpolder .............. 436/39 |
| 5,229,295 A | | 7/1993 | Travis ................. 436/39 |

* cited by examiner

Primary Examiner—Daniel S. Metzmaier
(74) Attorney, Agent, or Firm—Arthur M. Peslak, Esq.

(57) ABSTRACT

A visual indicating paste composition for detecting of aqueous solutions in hydrocarbons by changes in color. The paste is utilized by placing on a probe and inserting the probe in a storage device for fuel. Said paste comprising:

a) a liquid carrier selected from high molecular weight polyols;
  b) a caustic powder selected from alkaline earth oxides;
  c) a gelling agent;
  d) a surfactant consisting of ethoxylated nonylphenol with 9 moles of ethylene oxide;
  e) a filler material.
  f) a water scavenger consisting of aluminum isopropoxide;
  g) an indicator dye; and
  h) a neutral dye;

wherein the paste of the present invention will change color upon contact with an aqueous solution in the pH range of about between 7 and 11.

10 Claims, No Drawings

COMPOSITION AND PROBE FOR DETECTION OF WATER

BACKGROUND OF THE INVENTION

The present invention is directed to a visual indicating paste composition utilized to detect the presence. and particularly the level, of aqueous solutions when admixed with hydrocarbons such as gasoline, oil or other fuel and petroleum fractions. More particularly, the invention is concerned with a visual indicating paste composition which is capable of undergoing a change in color upon contact with aqueous solutions which may be present in minor amounts. generally as a separate phase. in hydrocarbon storage tanks, delivery vehicles, distribution systems, and any other systems for the same purpose. The composition of the invention is particularly adapted for use in determining the water level in the bottom of gasoline storage and transportation tanks to determine the amount of free water resting in a tank that is partially filled with hydrocarbon, and when the water contains oxygenated blending components with gasoline, such as alcohol and ethers. Also the composition of the invention is particularly adopted for use in determining the water level in the bottom of turbine fuel storage and transportation tanks to determine the amount of water resting in the tank partially filled with hydrocarbon. In addition, the paste is particularly useful when the water contains Fuel System Icing Inhibitor (FSII) mixed with Turbine Aviation Fuel, such as Ethylene Glycol Monomethyl Ether (EGME and Diethylene Glycol Monomethyl Ether (DiEGME).

OBJECTS AND SUMMARY OF THE INVENTION

Accordingly, an object of the present invention is to provide a visual indicating paste composition which will, upon contact with aqueous solutions. produce a clear detectable color change.

Another object of the invention is to provide a visual indicating paste for producing a sharp and distinct color change upon contact with aqueous solutions without bleeding, and which reacts rapidly with water admixed with hydrocarbon.

Still another object of the invention is to provide a visual indicating paste with low solubility in aqueous solutions and hydrocarbons. In addition, the paste will have a long shelf life, low hygroscopicity and good adhesion to the substrate to which it is applied during use.

Still another object is to provide a visual indicating composition which is useful for locating the water level of aqueous solutions containing oxygenated blending components in the bottom of tanks and delivery systems containing hydrocarbons such as gasoline, and particularly for indicating sharp and distinct color changes without bleeding or running off the probe to which the paste will be applied.

Still another object is to provide a visual indicating composition paste for producing a sharp color change upon contact with an aqueous solution containing anti-icing additive, which is often mixed with Turbine Fuel Oil. These and other objects, features and advantages of the invention will be apparent from the specification.

DETAILED DESCRIPTION OF THE INVENTION

The present invention is directed to a composition for a paste for detecting the presence of water in storage devices for hydrocarbon fuels. It is presently contemplated that the paste will be used in the conventional manner of applying the paste to a probe which will be inserted into the storage device, withdrawn therefrom, and visually inspected for a color change in the paste. Such a color change would indicate the presence of water in the storage device.

It has been discovered, after testing a number of combinations of materials that a particular composition comprised of an indicator capable of changing color in the pH range between about 7 and 11 and certain inorganic bases dispersed in a liquid carrier will provide considerable improvement in effectiveness over commercially available pastes. The paste of the present invention is an improvement of over prior pastes in that it produces a detectable color change upon contact with such admixtures, and particularly aqueous solutions containing oxygen-containing organic compounds such as lower alkanols and ethers. In formulating the composition of the present invention, a selected dye is dispersed together with a solid inorganic base in the form of caustic powder which is substantially insoluble in the liquid carrier for the composition. The liquid carrier is capable of absorbing water but is not readily leached by the aqueous solution or hydrocarbon. Specifically, it has been found that employment of a particular class of insoluble bases such as alkaline earth oxide, hydroxide. or mixtures thereof, and preferably calcium oxide. in the compositions of the invention provides a visual paste indicating composition meeting the above-specified objects of the invention.

As the vehicle for the paste composition of the invention, there is employed a liquid carrier, which is capable of absorbing water without being readily, leached by water or hydrocarbons. Also the liquid carrier has to be of a sufficiently high viscosity to create proper consistency of the resulting paste. Preferably, high molecular weight polyols are used. Some examples of the liquid carrier are the polyols with molecular weight higher than 100 grams/moles, such as; dipropylene glycol and tripropylene glycol. Usually the liquid carrier is employed in an amount between 40 and 50% by weight. Best results have been obtained when using polyalkylene glycols in an amount of about 45% by weight.

The caustic powder employed as a constituent of the paste in the present invention must be one which does not dissolve and ionize in the liquid carrier, but is readily soluble in water. Typical caustic powders for the paste of this invention are earth oxides. preferably calcium oxide. The caustic powder is employed in a concentration ranging from 10 to 15% by weight. for best results.

A gelling agent is used as thickener for the paste and to gel the composition. Fumed colloidal silica products, in a concentration ranging from 4 to 6% weight provide best results. Without the gelling agent, in time. part of the glycol will separate from the composition forming a liquid layer on top of the paste.

To improve the overall performance of the paste of the present invention. a surfactant IGEPAL CO-630 is used. which eliminates spottiness. decreases the immersion time and results in a clear and distinct color cut. IGEPAL, CO-630 is an ethoxylated nonylphenol with 9 moles of ethylene oxide. It is an outstanding water-soluble surface modifling surfactant. It is an excellent wetting agent and emulsifier for aromatic solvents. which makes it the preferred surfactant for the composition of the present invention. The surfactant liquid is employed in a concentration ranging from 1 to 4% by weight.

Calcium Carbonate is used as a filler material in the paste of the present invention. Calcium Carbonate increases the pH of the composition and results in the optimum hydrophilic/hydrophobic balance of the paste of the present invention. The optimum concentrations for the filler range from 25 to 35 % by weight.

A small amount of Aluminum Isopropoxide is added to the paste of the present invention. The presence of Aluminum Isopropoxide in the paste results in considerable improvement in shelf life and water tolerance. Due to the fact that Aluminum Isopropoxide acts as a water scavenger, the shelf life of the paste of the present invention is greatly increased over that of prior pastes. The Aluminum Isopropoxide is employed in the paste composition in an amount sufficient to provide the desired stabilization and inhibition to moisture. Preferably Aluminum Isopropoxide should be present in a concentration ranging from 1.5 to 4 percent by weight. Aluminum Isopropoxide decomposes in water to Aluminum hydroxide and isopropanol. Aluminum hydroxide is a very weak base, which does not appreciably affect the pH of an aqueous solution. However, the isopropanol is an alcohol having weak acidity which helps prevent the color change of the paste for a longer period of time than prior pastes during storage. Thus the shelf life of the paste of the present invention is increased. In the absence of such a water scavenger, the paste will change color over a short period of storage time due to moisture in the air.

In use. the paste of the present invention changes color within about 30 seconds, normally within 10 to 15 seconds. depending on the indicator dye employed. The paste produces a sharp color change even in aqueous liquids, which contain 98% of an oxygenated hydrocarbon. Oxygenated hydrocarbons are typically obtainable from the use of oxygenated blending components, that are leached from the hydrocarbon fuel into the water. Therefore it is very important to have an accurate reading for different concentrations of the oxygenated hydrocarbons in the aqueous liquids, which is one of the strengths of the present invention.

The indicator dye employed in the composition of the present invention are water soluble dyes as fine anhydrous crystalline powders, which are available from commercial sources. These dyes are characterized as being capable of changing the color of the paste composition in the range of pH between 7 and 11. Usually these dyes are employed in concentrations sufficient to provide the desired color change. The concentration of the dye is preferably between 1 and 5 percent by weight. Representative for these types of dyes is the Phenolphthalein. It is very important to have a sharp, clear cut color change since the paste is used for storage tanks containing excessive quantities of dirt, rust or other dark colored materials or debris. The paste of the present invention exhibits very good color contrast between the light green and the dark purple color of the paste after having been immersed in the aqueous liquid.

A green neutral dye is used to give the paste a light green color prior to use. It has been found that the contrast between the light green and purple upon contact with an aqueous solution is very distinctive and easy to see even in very dark or dirty environments. The powder dye is employed in a concentration ranging from 0.5 to 1% by weight.

It has also been discovered that a large contribution to the quality of the paste is provided by the method of preparation of the composition. Therefore the components should be fed to a mixer in a precise order to assure best homogeneity and consistency of the paste in the present invention. The order of mixing is:

1. Liquid carrier (Glycols)
2. Surfactant
3. Indicator dye
4. Neutral dye
5. Water scavenger (Aluminum Isopropoxide)
6. Caustic Powder (Calcium Oxide)
7. Gelling agent
8. Filler material (Calcium Carbonate)

The paste of the present invention is different form any other paste used in the industry. Starting from the composition—it has two new and unique components i.e. *i Aluminum Isopropoxide and IGEPAL* CO-630. In addition, the paste of the present invention is different than prior pastes because of the overall performance, long shelf life, reduced time of immersion, and excellent performance in aqueous liquids which contain a high percentage of oxygenated blending components for (Gasoline and Turbine Aviation Fuel.

Those of ordinary skill in the art will recognize that the embodiments just described merely illustrate the principles of the present invention. Many modifications may be made thereto without departing from the spirit and scope of the invention as set forth in the following claims.

What is claimed is:

1. A composition for a paste utilized to detect the presence and level of aqueous solutions admixed with hydrocarbons comprising:
    a) a liquid carrier selected from high molecular weight polyols;
    b) a caustic powder selected from alkaline earth oxides;
    c) a gelling agent;
    d) a surfactant consisting of ethoxylated nonylphenol with 9 moles of ethylene oxide;
    e) a filler material;
    f) a water scavenger consisting of aluminum isopropoxide;
    g) an indicator dye; and
    h) a neutral dye;
wherein the paste of the present invention will change color upon contact with an aqueous solution in the pH range of about between 7 and 11.

2. The composition of claim 1 wherein the liquid carrier is either dipropylene glycol or tripopylene glycol and is present in the composition in the range of about 40 to 50% by weight.

3. The composition of claim 2 wherein the liquid carrier is present in an amount of about 45% by weight.

4. The composition of claim 2 wherein the caustic powder is calcium oxide and is present in the composition in the range of about 10 to 15% by weight.

5. The composition of claim 4 wherein the gelling agent is fumed colloidal silica and is present in the composition in the range of about 4 to 6% by weight.

6. The composition of claim 5 wherein the surfactant is present in the composition in the range of about 1 to 4% by weight.

7. The composition of claim 6 wherein the filler material is calcium carbonate and is present in the composition in the range of about 25 to 30% by weight.

8. The composition of claim 7 wherein the water scavenger is present in the composition in the range of about 1.5 to 4% by weight.

9. The composition of claim 8 wherein the indicator dye is phenolphthalein and is present in the composition in the range of about 1 to 5% by weight.

10. The composition of claim 9 wherein the neutral dye is a light green dye present in the composition in a range of about 0.5 to 1% by weight.

* * * * *